(12) United States Patent
Adanny et al.

(10) Patent No.: US 9,108,036 B2
(45) Date of Patent: *Aug. 18, 2015

(54) METHOD AND APPARATUS FOR FRACTIONAL SKIN TREATMENT

(71) Applicant: SYNERON MEDICAL LTD., Yoqneam Illit (IL)

(72) Inventors: Yossef Ori Adanny, Mitzpe (IL); Genady Nahshon, Binyamina (IL); Baruch Levine, Afula (IL); Avner Rosenberg, Beit-Shearim (IL)

(73) Assignee: SYNERON MEDICAL LTD., Yoqneam Illit (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/305,080

(22) Filed: Jun. 16, 2014

(65) Prior Publication Data

US 2014/0296852 A1    Oct. 2, 2014

Related U.S. Application Data

(63) Continuation of application No. 13/400,434, filed on Feb. 20, 2012, which is a continuation of application No. 12/505,576, filed on Jul. 20, 2009, now Pat. No. 8,357,150.

(51) Int. Cl.
| | | |
|---|---|---|
| *A61B 18/14* | (2006.01) | |
| *A61N 5/00* | (2006.01) | |
| *A61B 18/12* | (2006.01) | |
| *A61B 18/18* | (2006.01) | |
| *A61B 18/00* | (2006.01) | |

(52) U.S. Cl.
CPC .............. *A61N 5/00* (2013.01); *A61B 18/1233* (2013.01); *A61B 18/14* (2013.01); *A61B 18/18* (2013.01); *A61B 2018/0047* (2013.01); *A61B 2018/00452* (2013.01); *A61B 2018/00577* (2013.01); *A61B 2018/00589* (2013.01); *A61B 2018/00642* (2013.01); *A61B 2018/00702* (2013.01); *A61B 2018/00827* (2013.01); *A61B 2018/00875* (2013.01); *A61B 2018/1467* (2013.01)

(58) Field of Classification Search
USPC .......................................... 606/32–35, 41–50
See application file for complete search history.

(56) References Cited

U.S. PATENT DOCUMENTS

| | | | |
|---|---|---|---|
| 4,200,104 A | * | 4/1980 | Harris ............................ 606/35 |
| 4,844,063 A | | 7/1989 | Clark |
| 5,319,363 A | | 6/1994 | Welch et al. |
| 5,383,874 A | | 1/1995 | Jackson et al. |

(Continued)

FOREIGN PATENT DOCUMENTS

| | | |
|---|---|---|
| EP | 0569670 A2 | 11/1993 |
| EP | 1852060 A1 | 11/2007 |

OTHER PUBLICATIONS

Guidelines for Limiting Exposure to Time-Varying Electric, Magnetic, and Electromagnetic Fields (Up to 300 GHz), International Commission on Non-Ionizing Radiation Protection, ICNIRP Guidelines, Apr. 1998, vol. 74, No. 4, pp. 496-522.

*Primary Examiner* — Michael Peffley
(74) *Attorney, Agent, or Firm* — Finnegan, Henderson, Farabow, Garrett & Dunner LLP

(57) ABSTRACT

An apparatus for cosmetic RF skin treatment where the RF energy supply is isolated from the patient treated, such that in course of treatment no undesired current flows through the subject body.

28 Claims, 7 Drawing Sheets

(56) References Cited

U.S. PATENT DOCUMENTS

| | | |
|---|---|---|
| 5,681,282 A | 10/1997 | Eggers et al. |
| 5,755,753 A | 5/1998 | Knowlton |
| 5,873,855 A | 2/1999 | Eggers et al. |
| 6,024,733 A * | 2/2000 | Eggers et al. ............... 604/500 |
| 6,148,232 A | 11/2000 | Avrahami |
| 6,413,255 B1 | 7/2002 | Stern |
| 6,440,121 B1 | 8/2002 | Weber et al. |
| 6,597,946 B2 | 7/2003 | Avrahami et al. |
| 6,611,706 B2 | 8/2003 | Avrahami et al. |
| 6,702,808 B1 | 3/2004 | Kreindel |
| 6,708,060 B1 | 3/2004 | Avrahami et al. |
| 7,022,121 B2 | 4/2006 | Stern et al. |
| 7,164,942 B2 | 1/2007 | Avrahami et al. |
| 7,435,247 B2 | 10/2008 | Woloszko et al. |
| 7,494,488 B2 | 2/2009 | Weber |
| 8,216,215 B2 | 7/2012 | Flyash et al. |
| 2004/0210214 A1 * | 10/2004 | Knowlton ....................... 606/41 |
| 2007/0191827 A1 * | 8/2007 | Lischinsky et al. ............. 606/34 |
| 2008/0188846 A1 * | 8/2008 | Palanker et al. ................ 606/32 |
| 2008/0214988 A1 | 9/2008 | Altshuler et al. |
| 2009/0054743 A1 | 2/2009 | Stewart |
| 2009/0105706 A1 | 4/2009 | Livneh |
| 2010/0198216 A1 * | 8/2010 | Palanker ........................ 606/41 |

* cited by examiner

METHOD AND APPARATUS FOR FRACTIONAL SKIN TREATMENT

CROSS-REFERENCE TO RELATED REFERENCES

This application is a continuation of U.S. application Ser. No. 13/400,434, filed on Feb. 20, 2012, which is a continuation of U.S. application Ser. No. 12/505,576, filed on Jul. 20, 2009, now issued as U.S. Pat. No. 8,357,150. The contents of these priority applications are incorporated herein by reference. This application is related to U.S. application Ser. No. 12/324,932, filed Nov. 28, 2008, now issued as U.S. Pat. No. 8,216,215, which is incorporated herein by reference.

TECHNOLOGY FIELD

The method and apparatus generally relate to skin treatment procedures and in particular to cosmetic skin resurfacing and rejuvenation procedures.

BACKGROUND

Fractional skin resurfacing or rejuvenation is a recently developed skin ablative technology. There are two types of devices used to ablate the skin: laser based devices and RF based devices. Both types of these devices ablate a pattern of extremely small diameter shallow holes or zones. The holes are microscopically small treatment zones surrounded by untreated skin areas. The treatment results in a very rapid healing or recovery and skin resurfacing of the treated. In the healing process of the treated zones, a layer of new skin appears, restoring a fresh, youthful complexion.

The pattern of small holes is typically produced by an X-Y scanning laser beam or by application of RF energy or voltage. The laser is focused on the skin and usually operates in pulse mode ablating micron size holes in the skin.

RF based fractional skin treatment produces a scanning pattern of micron size holes in the skin a similar to laser. Typically, the energy is delivered to the skin by an applicator equipped by a tip having a plurality of voltage to skin applying/delivering elements or contact elements arranged in a matrix or in an array. The voltage to skin applying elements are placed in contact with the segment of the skin to be treated and driven by a source of suitable power and frequency RF energy. Application of a high voltage RF pulse to the electrodes ablates the skin under the respective electrode forming a small hole.

In some instances application of laser or RF voltage pulses causes discomfort and even pain to the treated subject, although the experience based on the individual and as such, the pain sensation may be different from subject to subject. In other instances there may be a difference in the size of micro holes formed by the applicator at the same treatment session. Healing of larger size holes may take a longer period of time than the healing process for smaller size holes and in some instances, the larger holes may tend to result in causing damage to the skin rather than producing the desired skin effect.

In order to soften the discomfort and lessen the pain and other side effects associated with the fractional treatment, practitioners have started using topically applied lidocaine cream or even oral sedation.

Fractional skin treatment is applicable in the correction of almost all cosmetic skin defects such as signs of aging, wrinkles, discolorations, acne scars, tatoo removal, and other skin defects. The cost of the RF based products is lower than that of the products operating with laser radiation and they will most probably become widely used if the discomfort and occasional pain associated with their use could be eliminated.

US Patent Application Publication No. 2006/0047281 and U.S. patent application Ser. No. 12/324,932 to the same assignee disclose RF based products such as eMatrix™ suitable for fractional skin treatment.

GLOSSARY

In the context of the present disclosure "RF voltage" and "RF energy" are used interchangeably and have the same meaning. The mathematical relationship between these two parameters is well known and knowledge of one of them allows easy determination of the other.

In the context of the present disclosure "skin resistance" and "skin impedance" are used interchangeably and have the same meaning. The mathematical relation between these two parameters is well known and knowledge of one of them allows easy determination of the other.

The term "desired skin effect" as used in the present disclosure means a result of RF energy application, which may be wrinkle removal, hair removal, collagen shrinking or destruction, skin rejuvenation, and other cosmetic and skin treatments.

The term "plateau" of a function is a part of its domain where the function has constant value.

BRIEF SUMMARY

An apparatus for cosmetic RF skin treatment where the RF energy supply is isolated from the subject treated, such that in course of treatment no undesired current flows through the subject body. The apparatus includes an applicator with a tip that is populated by a plurality of voltage applying dome shaped elements protruding from the tip surface and organized in one common cluster and a cluster of electrodes bounding the dome shaped elements and having an area larger than the dome shaped elements have. The apparatus applies voltage to the elements with a magnitude sufficient to cause a desired skin effect. A current limiter limits the RF induced current thereby preventing skin damage. The apparatus continuously senses the treated skin segment impedance and varies the RF energy at a low skin impedance and/or stops the pulse in cases of too low or too high skin impedance.

DETAILED DESCRIPTION OF EXEMPLARY EMBODIMENTS

The principles and execution of the method and the apparatus may be better understood with reference to the drawings and the accompanying description of the non-limiting, exemplary embodiments, shown in the Figures.

Figure 1A:
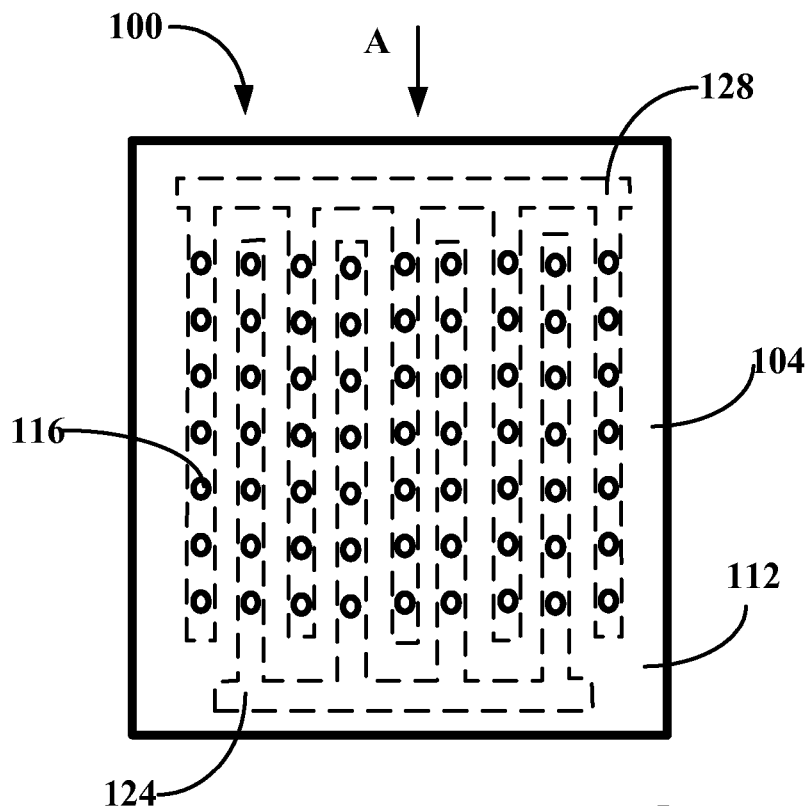
FIGS. 1A and 1B, collectively referred to as FIG. 1, are schematic illustrations of a prior art RF applicator tip for fractional skin treatment.
Figure 1B:
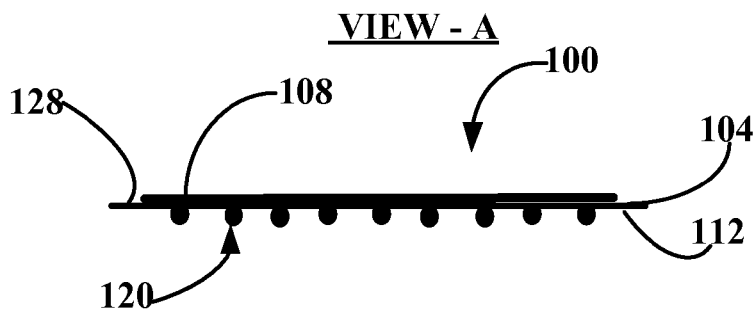

Reference is made to FIG. 1, which is a schematic illustration of a prior art RF applicator tip for fractional skin treatment disclosed in the U.S. patent application Ser. No. 12/324, 932 to the same assignee. A carrier 100 on which voltage to skin delivering elements or contact elements are formed may be a flexible or rigid article made of a polyimide film or similar material, with an exemplary thickness range of 0.5 mil to 6 mil (12.5 micron to 150 micron). The term "carrier" in the context of the present disclosure means a substrate having an array of voltage to skin application elements, a two dimensional array or matrix of voltage to skin application elements. Substrate 104 has on one of its surfaces 112 an array or matrix of miniature (microscopic), discrete, voltage to skin application elements 116 protruding from surface 112 and terminated by dome type shapes 120. A pattern of conductors 124 and 128 shown in broken lines arranged on the back or second side of substrate 104 enables addressing of all elements 116, a cluster of elements 116, or each of elements 116 individually. Carrier 100, having formed on it, the voltage to skin delivering elements is configured to allow quick attachment to an applicator and will be termed in the present document as a "tip" or an "applicator tip." An arrangement of RF contacts enabling connection to a source of radio frequency voltage is provided by forming on the back side of the carrier 104 contact points or strips 108 communicating with respective contact arrangements made in substrate 104. Voltage to skin delivering elements 116 are arranged in a symmetric pattern with all even rows 124 connected to one of the RF supply contact strips or ports 124 and all uneven rows 128 connected to another or second contact strip or RF supply port 128.

Figure 2:
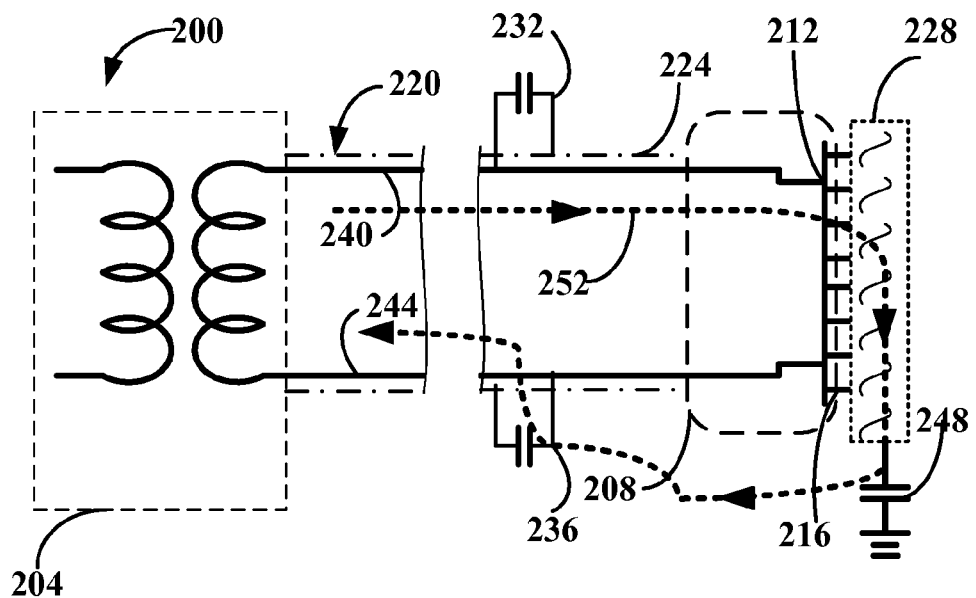
FIG. 2 is a schematic illustration of a prior art RF voltage supplying circuit for driving the RF applicator tip for fractional skin treatment.

FIG. 2 is a schematic illustration of a prior art RF voltage supplying circuit for driving the RF applicator tip for fractional skin treatment. A source of RF voltage 200 may be located in stand alone housing 204. Alternatively, the source of the RF voltage may be located in the applicator case 208 shown in broken lines. The source provides RF voltage to applicator tip 212, and in particular to voltage to skin delivering elements 216 through a shielded harness 220. Shield 224 is schematically shown in broken and doted lines. The length of the harness 220 is selected to enable convenient caregiver operation and may be one to two meters long, for example. There exists a certain parasitic capacitance 232 and 236 between the shield 224 and each of the RF current conducting lines 240 and 244. The treated subject has also certain capacitance 248. For skin treatment, tip 212 is placed in contact with a segment of the skin 228 to be treated. As a result of uneven contact of the voltage to skin delivering elements 216 organized into even 124 and uneven 128 rows or clusters with segment of the skin 228 to be treated, an undesired RF current path 252 may be formed. This current passes through the subject 228 and may cause a painful sensation and even an electric shock to the subject.

Figure 3A:
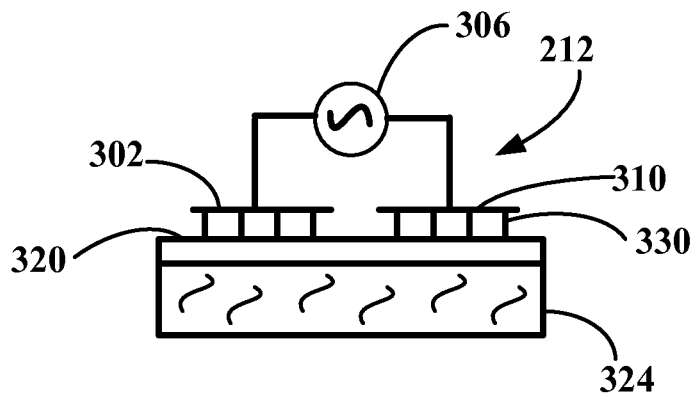
FIGS. 3A through 3C are schematic illustrations of an equivalent electric circuit of the tip for fractional skin treatment.

FIG. 3 is a schematic illustration of an equivalent electric circuit of the tip for fractional skin treatment 212 being in contact with the treated segment of the skin. FIG. 3A schematically shows the tip 212 with all contact elements 330 located in uneven rows 1, 3, 5, and 7 of the tip 212 collectively marked as 302 and shown as connected to a first RF port of RF voltage source 306 and all contact elements located in even rows 2, 4, 6, and 8 collectively marked as 310 and shown as connected to a second RF port of RF voltage source 306. All of the contact elements are in contact with the upper skin layer 320 for example, stratum corneum which has a relatively low conductivity, where numeral 324 marks dermis layer and even deeper skin layers that have a relatively high, as compared to stratum corneum, conductivity.

Figure 3B:
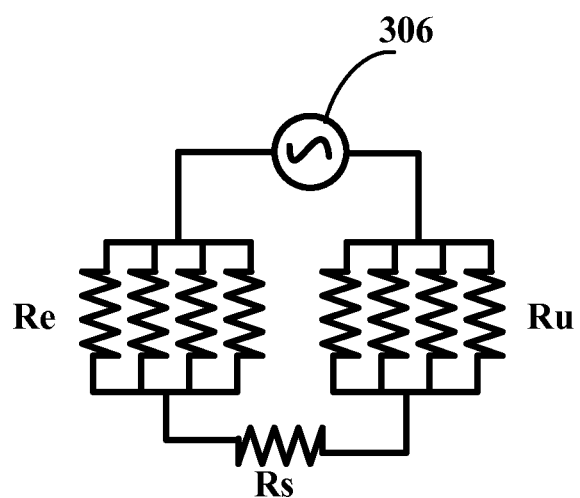
Figure 3C:
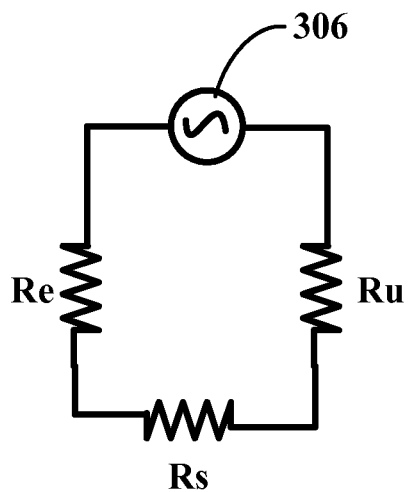

Referring to FIG. 3B, the electrical channel from each contact element through the low conductance skin layer is represented as a resistor (for the simplicity of the explanation channel capacitance is neglected). The high conductivity dermis is represented as a common resistor Rs. Further equivalent electric scheme simplification is shown in FIG. 3C, where all uneven resistors have been replaced by an equivalent resistor Ru and even rows resistors by Re. Typically, each of the individual contact element resistors is 50K-100K Ohms, therefore Ru and Re are about 2K Ohms each, whereas Rs is an order of magnitude smaller, about 200 Ohms and it can be neglected for the purpose of the discussion.

Because not all of the voltage to skin delivering elements or contact elements 330 (FIG. 3A) may be properly attached to the skin and some of them may bear some dirt and other residuals from the previous treatment, and different skin segments may have different resistance, there is a difference in the resistance to current passing through each of the contact elements and accordingly through the clusters (even or uneven clusters) they form. If the RF voltage or energy flows into any of the Ru or Re resistors, it increases its resistance it generates a positive feedback under which the larger resistor gets more energy than the smaller one, its resistance increases more rapidly, therefore it gets even more energy, and so on. The end result is that the one of Ru or Re clusters, which had initially greater value finally takes most of the energy and leaves a different imprint on the skin (for example, only contact elements located in even or uneven rows may leave an imprint). This reduces the efficacy of the treatment and generates undesired skin effects, excessive pain, and even electric shock.

In order to resolve this problem, as disclosed in the U.S. patent application Ser. No. 12/324,932 assigned to the same assignee, it is possible to address individually each contact element or pin and connect it to the source of voltage through a large impedance, which can be a resistor, a small capacitor, a large inductor, or a combinations of all of them. This would stabilize the RF induced current to each individual channel reducing the "competition" between the contact elements and clusters of contact elements. For sterilization and hygiene purposes use of disposable tips is preferred to the use of reusable tips. Addressing of each individual contact element however, complicates and increases manufacturing cost of such tips.

Another way to equalize the resistance or impedance of each contact element and reduce the pain sensation and potential electric shocks to the treated subject is to bring the skin by some initial treatment to an optimal and more uniform resistance value, which for example may be about 3000 Ohms. There will always be however, segments of skin where the resistance is low and any slight sweating may drive the skin to lower impedances.

Figure 4:
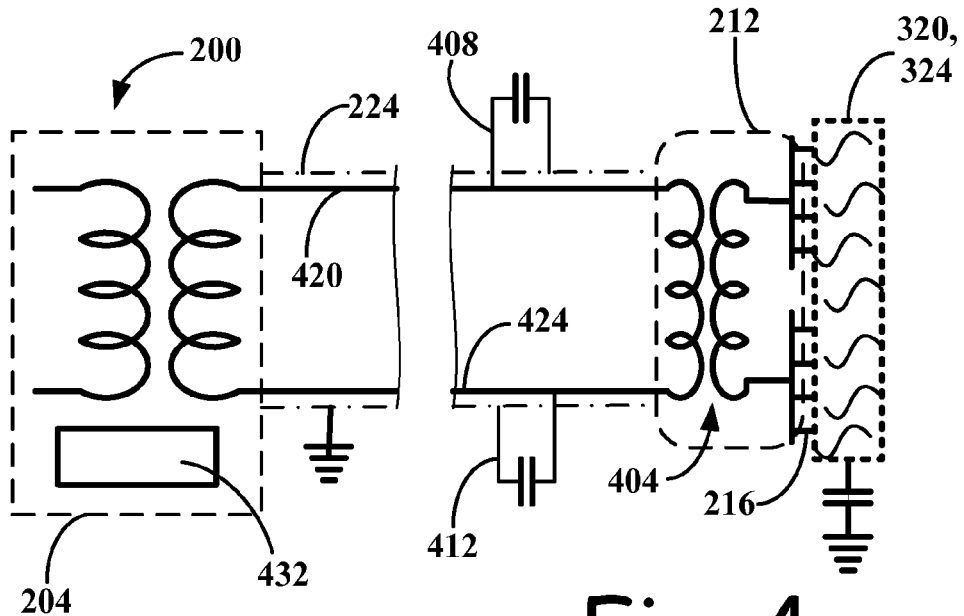
FIG. 4 is a schematic illustration of an exemplary embodiment of the present tip for fractional skin treatment driving circuit.

FIG. 4 is a schematic illustration of an exemplary embodiment of the present tip driving circuit. The embodiment of FIG. 4 eliminates or at least, greatly reduces the pain sensation and electric shock that could affect the treated subject. A low capacitance for example, 4 pF to 10 pF isolating transformer 404 is located in close proximity to the tip 212 with the voltage to skin delivering elements 216. In the course of operation, transformer 404 reduces or completely eliminates currents flowing through the subject body due to parasitic capacitances 408 and 412 formed by the subject skin 320, 324 and the ground and between the shield 224 and each of the RF conducting lines 420 and 424. A controller 432 governing operation of all of the apparatus devices may be located in housing 204. Controller 432 may have a processor, a memory, and other devices necessary for controlling the treatment process.

Figure 5:
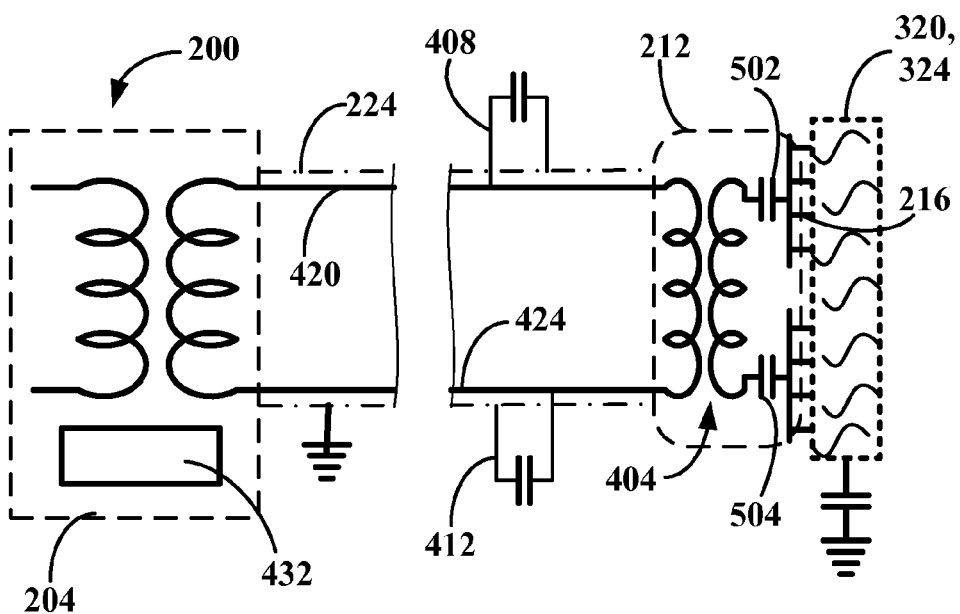
FIG. 5 is a schematic illustration of another exemplary embodiment of the present tip for fractional skin treatment driving circuit.

FIG. 5 is a schematic illustration of an additional exemplary embodiment of the present tip 212 driving circuit that eliminates, or greatly reduces, pain sensation and electric shock that could affect the treated subject. In addition to the low capacitance transformer 404 one or more capacitors 502 and 504 located in the current path and connected in series to the electrodes 216 form a high pass filter. In the course of apparatus operation, the high pass filter filters out the low frequency currents, to which the sensitivity of the treated subject is high, generated by plasma formed at the voltage to skin delivering elements 216 being in contact with the skin 320, 324 and flowing through the subject body in course of the apparatus/applicator operation. (reference can be made to Guidelines for Limiting Exposure to Time-Varying Electric, Magnetic, and Electromagnetic Fields up to 300 GHz; International Commission on Non-Ionizing Radiation Protection, Page 10.

Figure 6:
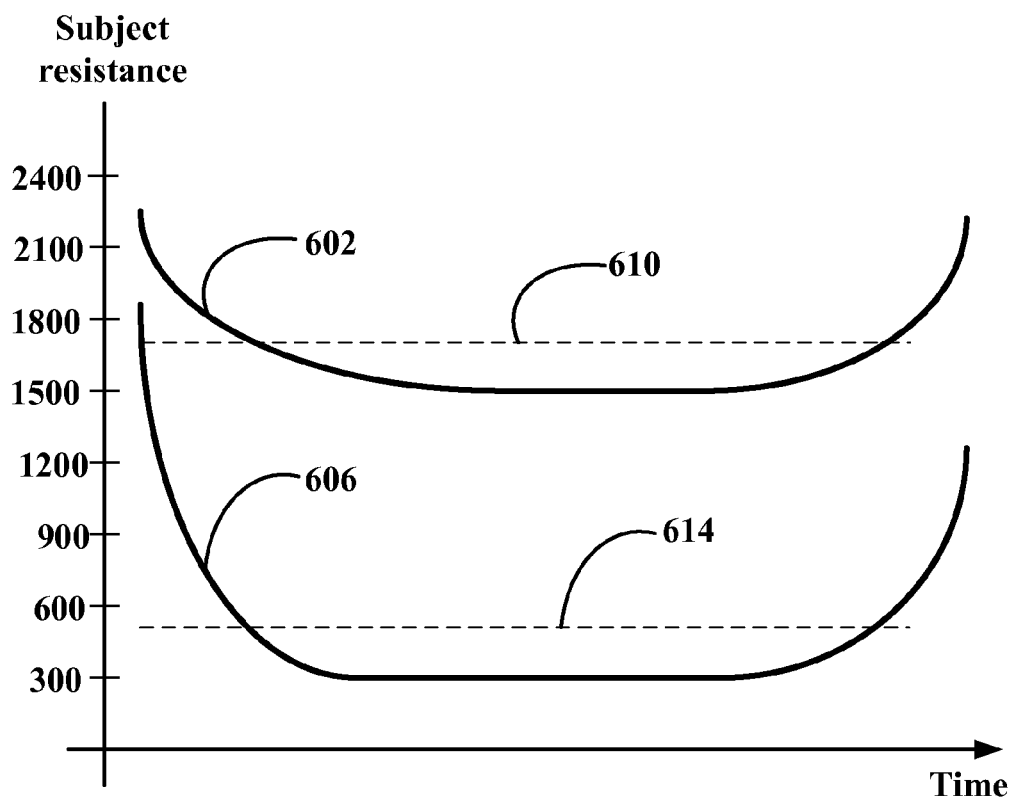
FIG. 6 is a schematic illustration of skin resistance variation under the application of an RF energy pulse.

Electrical resistance of skin differs from subject to subject and complicates proper RF energy value selection and application of the RF energy for cosmetic skin treatment. Further to this, resistance of the subject may vary under application of RF energy. FIG. 6 is a schematic illustration of skin resistance variation under the application of RF energy in a pulse mode. Lines 602 and 606 mark different skin behavior under an RF energy pulse and lines 610 and 614 mark the upper and lower skin resistance or impedance values that result in a desired skin effect, although because of the large variability of the treated subjects skin properties, there may be a need to set experimentally other values matching a particular subject properties. The length of the pulse, as will be explained later, may vary from few milliseconds to hundreds of milliseconds or even seconds.

In order to establish proper treatment parameters prior to the treatment, a system operator or user can calibrate the apparatus and operational treatment parameters derived as a result of the calibration are loaded into a look-up-table (LUT) that may be stored in the memory of the controller 432. For the purpose of calibration, a known variable resistance modeling the subject and the tip behavior is connected instead of a subject to the RF voltage supply. In one of the calibrations, a current flowing in the circuit at different RF voltages and different resistance value is recorded and in another calibration the RF energy applied to the variable resistance, modeling different skin impedance is recorded.

When skin is wet its resistance is low and with the application of the RF energy it continues to fall (line 606). Without being bound by a specific theory it is believed that most of the RF energy applied to the skin is initially wasted to dry the skin and when the skin under the influence of RF energy becomes dry, the skin resistance begins growing to higher values. Resistance increase is believed to be connected with vaporization, accompanied or followed by tissue ablation. It is considered a good treatment (desired skin effect) when ablation is created in the tissue below the electrodes.

It has been experimentally established that treatment resulting in a desired skin effect takes place when the resistance of the subject's skin is between Rlow and Rhigh, where the specific values depend on the number of electrodes in the tip and their arrangement and on the skin properties. For a typical tip shown in FIG. 1, with 64 electrodes and a diameter of 250 μm each, Rlow is about 1500 Ohms and Rhigh is about 4000 Ohms. For the asymmetrical tip of FIG. 8, Rlow is about 600 Ohms and Rhigh is about 1600 Ohms. When the skin resistance (or impedance) falls below the lower limit, most of the RF energy applied to the skin is wasted on drying the skin and not on causing the desired skin effect. Generally, the upper skin resistance limit is in the vicinity of the stratum corneum resistance with the lower limit corresponding to wet skin. When the skin resistance is within the indicated resistance limits, as shown by broken lines 610 and 614, application of RF to the skin through the voltage to skin delivering elements results in a desired skin effect. Continuous or pseudo continuous monitoring of the skin impedance during the RF pulse enables control of the energy delivered to skin. For example, when the resistance falls below the pre-set threshold of e.g. 600 Ohms, the time of the RF pulse may be increased by the control, until the control unit identifies or detects the beginning of an increase in the resistance. From the time that the beginning of the resistance increase is detected, the amount of energy delivered is either fixed or it takes into consideration the energy delivered up to that point, thereby allowing or ensuring the proper skin effect. It is also possible to cut off the RF pulses when the skin impedance is below a pre-set impedance or resistance value and notify operator, to exclude inefficient pulses. Another possibility is to notifying the operator on the low value of skin resistance and the need to dry out the skin. It is also possible to set the apparatus to deliver a pre-set amount of energy to the skin.

It is possible to generalize the skin behavior under an RF pulse into at least two typical cases, although a mixture of these cases and other skin behavior may be present: a) skin resistance remains high through all of the RF pulse application time and b) skin resistance drops down below the lower resistance limit and after it reaches (the function reaches) a plateau it begins to rise. Accordingly, by monitoring the current flowing in the voltage to skin delivering elements circuit, it is possible to set proper treatment parameters resulting in a desired skin effect and not causing adverse side effects such as pain, burnings and other. It was found that resistances above Rhigh correspond to dirty tip and/or are caused by improper attachment of the tip to the skin. In both cases, the pulses may cause undesired pain. In order to reduce the pain, current limiter 704 (FIG. 7) or a control system immediately cuts the pulse when the resistance is above a certain pre-set threshold. The control will notify the operator to check proper attachment of the tip to skin and/or clean the tip.

Figure 7:
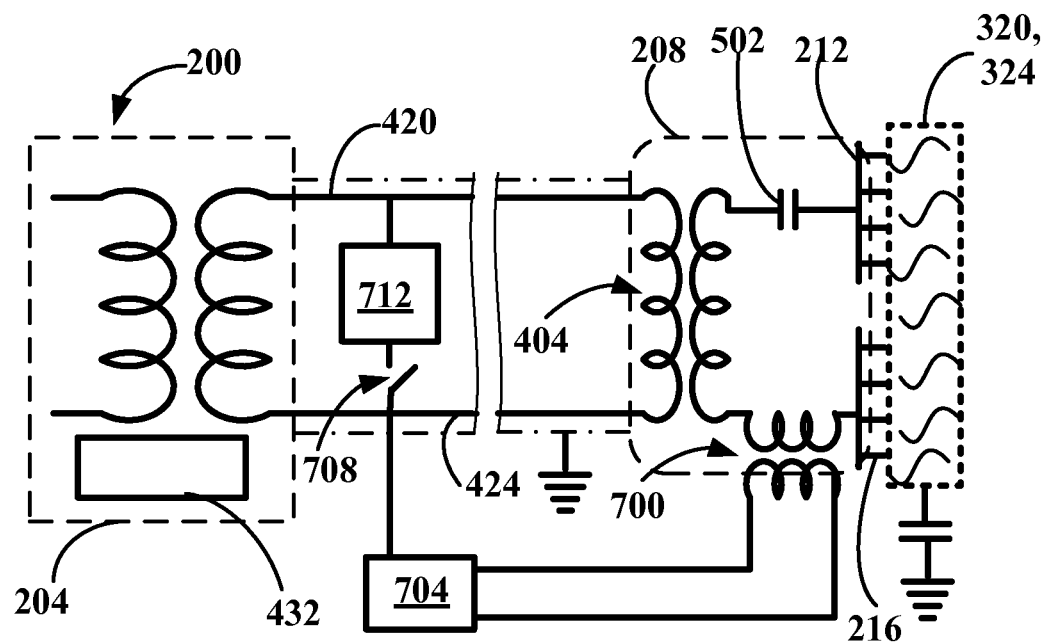
FIG. 7 is a schematic illustration of an exemplary embodiment of the present tip for fractional skin treatment control circuit.

FIG. 7 is a schematic illustration of another exemplary embodiment of the present tip for fractional skin treatment driving circuit that eliminates pain sensation and electric shock that could affect the treated subject. A sensing element 700 senses the current flowing in the immediate to the tip for fractional skin treatment circuit. The sensing and sampling may be continuous or performed at very short time intervals, for example every few tens of a microsecond. A fast response RF induced current limiter 704 in course of operation sets a maximum to the current which flows into the skin. Immediately, with the current increase above a pre-set value, it operates a fast switch 708 that closes the circuit directing the current to an energy absorbing element 712, which dissipates the excessive energy as heat. The RF energy absorbing element 712 may be packaged or even be a part of current limiter 704. The switch may be a bi-polar transistor, a MOSFET switch, an IGBT switch or any other fast switch. If the switch is operated in the analogue regime, it can stabilize the current to the pre-set maximum value or below that value. The energy absorbing element 712 may be a bank of resistors, bridge of diodes or similar devices. This protects the subject from electric shock, skin burn, and other potential treatment side effects.

Figure 8:
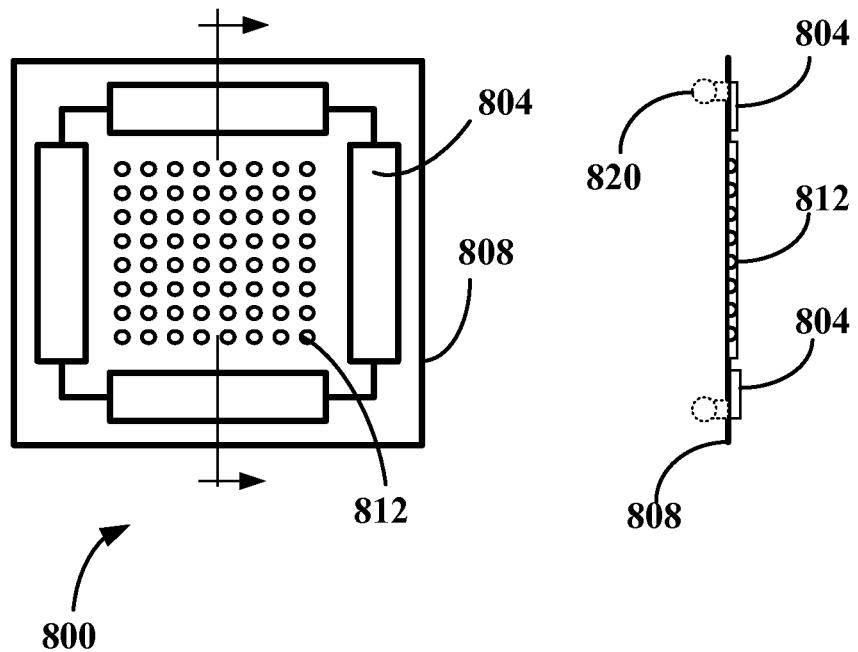
FIG. 8 is a schematic illustration of an exemplary embodiment of the present RF applicator tip for fractional skin treatment.

FIG. 1 illustrates a prior art tip, which is basically a symmetrical tip including even and uneven arrays of electrodes. FIG. 8 is a schematic illustration of an exemplary embodiment of the present RF applicator tip for fractional skin treatment that eliminates or significantly reduces the "competition" between the tip electrodes. Although the tip 800 is for a bi-polar treatment, it is an asymmetrical tip. Tip 800 has one or more (a cluster) large "ground" electrodes 804 located in the peripheral area of substrate 808 and connected to one RF output port. All of the miniature discrete, voltage to skin application elements 812 protruding from the substrate surface and terminated by dome type shapes are connected together to the other port of the RF output transformer. The particular tip has 64 elements, although other designs with different number of elements are possible. The further advantage of this solution is that the resistance variations may be more obvious since there is no competition between the electrodes located in the even and uneven contact strips, thus preventing the undesired partial imprint on the skin and the accompanied pain. The area of the voltage to skin application elements 804 is substantially larger than the area of the terminated by dome type shapes elements 812. Tip 800 possesses a mechanism 820 enabling quick removal and attachment of the tip to the applicator and RF voltage connection elements (not shown).

The electric scheme and the tip structure disclosed above eliminate electrical shock feeling, reduce or eliminate the pain associated with the treatment and increase the treatment efficacy. The isolating transformer is located very close to the application tip to reduce ground currents through parasitic capacitance. Series capacitors located in the path to the electrodes filter out low frequency currents which are produced by plasma formed at the electrodes and fast current limiter sets a maximum to the current which flows into the skin.

Typical operating parameters of the apparatus are:
Voltage on high impedance load: 850 Vp-p
Current: 50-400 mA
Pulse length: 10-150 msec
Energy per pulse (Actual energy delivered to the skin): 0.5-4 J, more typical 1-2 J.
Frequency of the RF: 1 MHz, although 100 kHz up to 10 MHz may be considered.
Typical control parameters for the asymmetrical tip, 64 pins, 250 microns each:
High resistance limit for cutting of pulses for pain reduction: >1600 Ohms (for 64 pins asymmetrical tip)
Low resistance limit for cutting low efficiency pulses: <200 Ohms (for 64 pins asymmetrical tip)
Range of resistance where control adds energy to dry the skin: 200-600 Ohms (for 64 pins asymmetrical tip)

We claim:

1. A skin treatment device, comprising:
an applicator tip;
a plurality of electrodes configured for contacting a stratum corneum layer of skin external to a patient's body, the plurality of electrodes including:
a plurality of voltage to skin elements of a first size, arranged in a cluster, and being further configured for connection to a circuit for delivering RF energy to cause fractional skin treatment; and
a plurality of electrodes sized substantially larger than the first size and arranged at a periphery of the cluster and spaced from the cluster, and wherein the cluster of voltage to skin elements are free of any portion of the larger sized electrode therebetween.

2. The skin treatment device of claim 1, wherein the plurality of voltage to skin elements are arranged in an array.

3. The skin treatment device of claim 1, wherein the plurality of voltage to skin elements are arranged in a matrix.

4. The skin treatment device of claim 1 wherein the plurality of voltage to skin elements are microscopic.

5. The skin treatment device of claim 1, wherein the plurality of voltage to skin elements protrude from the applicator tip.

6. The skin treatment device of claim 1, wherein the cluster of voltage to skin elements is arranged between at least two of the larger sized electrodes.

7. The skin treatment device of claim 1, wherein the plurality of larger electrodes are arranged on the applicator tip in a manner at least partially surrounding the cluster of voltage to skin elements.

8. The skin treatment device of claim 7, wherein a total of at least four larger electrodes are arranged about the cluster of voltage to skin elements.

9. The skin treatment device of claim 1, wherein the plurality of voltage to skin elements each have a domed shape.

10. The skin treatment device of claim 1, wherein the plurality of voltage to skin elements of a first size are further configured for connection to a circuit for delivering RF energy and configured to generate RF pulses of a voltage sufficient to fractionally ablate skin under the voltage to skin elements.

11. The skin treatment device of claim 10, wherein the plurality of voltage to skin elements of a first size are further configured for connection to a circuit configured to deliver RF pulses sufficient to form a small hole in the skin beneath each of the voltage to skin elements.

12. The skin treatment device of claim 1, wherein the cluster includes at least 64 voltage to skin elements.

13. The skin treatment device of claim 1, wherein the cluster of voltage to skin elements and the at least one larger electrode are arranged on a common substrate.

14. The skin treatment device of claim 1, wherein the plurality of voltage to skin elements of a first size are further configured for connection to a circuit that includes an isolating transformer configured to reduce ground currents.

15. The skin treatment device of claim 14, wherein the plurality of voltage to skin elements of a first size are further configured for connection to a circuit that further includes a capacitor serially connected between the isolating transformer and at least some of the voltage to skin elements.

16. The skin treatment device of claim 1, wherein the tip is configured for cosmetic skin treatment and for removable attachment to a source of the RF energy.

17. The skin treatment device of claim 1, wherein the plurality of voltage to skin elements of a first size are further configured for connection to a circuit that further includes an RF energy absorbing element configured to limit an amount of current flowing into skin.

18. The skin treatment device of claim 1, wherein the plurality of voltage to skin elements are arranged in a generally rectangular shape.

19. The skin treatment device of claim 1, wherein a diameter of each of the plurality of voltage to skin elements is on an order of 250 microns and configured to cause both coagulation and ablation of the skin.

20. The skin treatment device of claim 1, wherein the at least one larger electrode is elongated and extends along at least a portion of a peripheral edge of the cluster of voltage to skin elements, with a gap between the elongated larger electrode and the peripheral edge of the cluster.

21. A skin treatment device, comprising:

a housing; and at least one processor within the housing and configured to control RF energy supplied to a removable applicator tip having a plurality of electrodes configured for contacting a stratum corneum layer of skin external to a patient's body, the plurality of electrodes including:

a plurality of voltage to skin elements of a first size, arranged in a cluster, and being further configured for connection to a circuit for delivering RF energy to cause fractional skin treatment; and a plurality of electrodes sized substantially larger than the first size and arranged at a periphery of the cluster and spaced from the cluster, and wherein the cluster of voltage to skin elements are free of any portion of the larger sized electrode therebetween;

wherein the at least one processor is configured to control RF energy in a manner such that energy is applied to the stratum corneum layer through the plurality of voltage to skin elements of the first size, and such that energy is collected from the stratum corneum on the at least one electrode sized substantially larger than the first size and arranged at a periphery of the cluster and spaced from the cluster.

22. The skin treatment device of claim 21, wherein the cluster of voltage to skin elements is arranged between at least two of the larger sized electrodes.

23. The skin treatment device of claim 21, wherein at least four larger electrodes are arranged about the periphery of the cluster.

24. The skin treatment device of claim 21, wherein the plurality of voltage to skin elements include at least 64 voltage to skin elements.

25. The skin treatment device of claim 21, wherein the circuit for delivering RF energy is configured to generate RE pulses of a voltage sufficient to fractionally ablate skin under the voltage to skin elements.

26. The skin treatment device of claim 21, wherein the circuit is configured to deliver RF pulses sufficient to form a small hole in the skin beneath each of the voltage to skin elements.

27. The skin treatment device of claim 21, wherein the removable applicator tip is configured for cosmetic skin treatment and for removable attachment to a source of the RF energy.

28. The skin treatment device of claim 21, wherein the plurality of voltage to skin elements are arranged in a generally rectangular shape.

* * * * *